US011097093B2

(12) United States Patent
Garrigue et al.

(10) Patent No.: US 11,097,093 B2
(45) Date of Patent: Aug. 24, 2021

(54) METHOD FOR MANAGING A CARDIAC PUMP

(71) Applicant: FINEHEART, Pessac (FR)

(72) Inventors: Stéphane Garrigue, Begles (FR); Arnaud Mascarell, Montbazon (FR)

(73) Assignee: FINEHEART, Pessac (FR)

( * ) Notice: Subject to any disclaimer, the term of this patent is extended or adjusted under 35 U.S.C. 154(b) by 161 days.

(21) Appl. No.: 16/320,717

(22) PCT Filed: Jul. 26, 2017

(86) PCT No.: PCT/FR2017/052093
§ 371 (c)(1),
(2) Date: Jan. 25, 2019

(87) PCT Pub. No.: WO2018/020161
PCT Pub. Date: Feb. 1, 2018

(65) Prior Publication Data
US 2019/0160214 A1 May 30, 2019

(30) Foreign Application Priority Data

Jul. 26, 2016 (FR) ...................................... 1657188

(51) Int. Cl.
*A61M 1/10* (2006.01)
*A61M 60/50* (2021.01)
(Continued)

(52) U.S. Cl.
CPC .......... *A61M 60/50* (2021.01); *A61M 60/148* (2021.01); *A61M 60/562* (2021.01);
(Continued)

(58) Field of Classification Search
CPC .. A61M 1/1086; A61M 1/1005; A61M 1/122; A61M 2205/3317; A61M 2205/50;
(Continued)

(56) References Cited

U.S. PATENT DOCUMENTS

| 6,066,086 A | 5/2000 | Antaki et al. |
| 2008/0133006 A1 | 6/2008 | Crosby et al. |

(Continued)

FOREIGN PATENT DOCUMENTS

WO  WO 2013/014339  1/2013

OTHER PUBLICATIONS

International Search Report, PCT/FR2017/052093, dated Nov. 8, 2017.

*Primary Examiner* — Rex R Holmes
(74) *Attorney, Agent, or Firm* — Nixon & Vanderhye

(57) ABSTRACT

In a method for managing a cardiac pump intended to assist the heart of a patient, the cardiac pump sends pressurized blood at a flow rate proportional to the speed of rotation Vrpm of the pump through the aortic valve of the heart. The steps, during a same ventricular systole, include: detecting mitral valve closure, rotational speed Vrpm of the pump being strictly less than a maximum value Vrpm max, increasing Vrpm of the pump such that, at time t2, after the time t corresponding to the closing of the mitral valve, the speed of rotation of the pump is equal, or substantially equal, to the maximum value Vrpm max of the speed of rotation, and keeping the speed of rotation Vrpm of the pump at this maximum value Vrpm max for at least a portion of the time period T during which the aortic valve is open.

17 Claims, 2 Drawing Sheets

(51) Int. Cl.
 *A61M 60/148* (2021.01)
 *A61M 60/562* (2021.01)
 *A61B 5/055* (2006.01)
 *A61B 6/00* (2006.01)
 *A61B 8/08* (2006.01)

(52) U.S. Cl.
 CPC ............... *A61B 5/055* (2013.01); *A61B 6/503* (2013.01); *A61B 8/0883* (2013.01); *A61M 2205/3317* (2013.01); *A61M 2205/3365* (2013.01); *A61M 2205/50* (2013.01); *A61M 2230/04* (2013.01)

(58) Field of Classification Search
 CPC ...... A61M 2230/04; A61M 2205/3365; A61B 6/503; A61B 8/0883; A61B 5/055
 See application file for complete search history.

(56) References Cited

U.S. PATENT DOCUMENTS

| | | | | |
|---|---|---|---|---|
| 2010/0268334 | A1* | 10/2010 | Pate | A61M 1/101 623/3.14 |
| 2011/0178361 | A1* | 7/2011 | Yomtov | A61M 1/1086 600/16 |
| 2014/0323796 | A1* | 10/2014 | Medvedev | A61M 1/1086 600/17 |
| 2016/0206797 | A1 | 7/2016 | Karch | |

\* cited by examiner

METHOD FOR MANAGING A CARDIAC PUMP

CROSS-REFERENCE TO RELATED APPLICATIONS

This application is a national stage of PCT/FR2017/052093, filed Jul. 26, 2017, which claims priority from FR 1657188, filed Jul. 26, 2016.

BACKGROUND OF THE INVENTION

Field of the Invention

The present invention relates to a method for managing an implantable cardiac pump, which is intended to assist a weakened ventricle of an individual, during the systolic phase.

Technological Background

Cardiac insufficiency (CI), is a pathological state in which the heart of a patient exhibits an incapacity to supply a blood flow necessary to the metabolic needs of the organism.

To treat cardiac insufficiency, it is known practice to implant a ventricular assistance device (VAD), which is an artificial cardiac pump.

This mechanical pump does not replace the heart which continues to operate, but adds an aid to the weakened ventricle in order to increase the blood flow in a way suited to the needs of the individual.

This assistance can be temporary pending an available graft to perform a heart transplant.

However, a significant proportion of patients who do not receive such a graft is observed, either because they cannot be candidates for such a transplant, for example because of a severe cardiac insufficiency, or because no suitable graft is available for these patients.

In this case, the ventricular assistance is used as end product, that is to say that the artificial cardiac pump is implanted long term.

These cardiac pumps are the object of intense research aiming to enhance the survival and the quality of life of the patients exhibiting a cardiac insufficiency.

Many advances have been made in recent years and ventricular assistance devices are now known that are more compact, silent and offer an increased service life.

The implantable cardiac pumps of the state of the art are thus typically equipped with an integrated electric motor to ensure the operation thereof, the speed of rotation of the pump supplying the necessary force to circulate the blood from the weakened ventricle to the bodily circulation.

The controller and the power source of the cardiac pump are typically placed outside the patient. A percutaneous line at the abdomen then ensures the link between the pump fixed to the wall of the ventricle and these external elements.

Although representing a certain measure of progress for the quality of life of a patient suffering from cardiac insufficiency, many drawbacks are still observed.

First of all, the patient is limited in his or her mobility by the presence of an external unit to which he or she is permanently linked. Showers and baths are not always allowed. And above all, risks of infection are likely to occur at the orifice of passage of the percutaneous line.

It is therefore sought to have the cardiac pump as independent as possible and implanted with its controller and its power source.

The individual affected by cardiac insufficiency will thus have his or her bodily integrity restored and will gain in mobility.

The patent application WO2013014339 A1 in the name of the present applicant describes an electric cardiac pump that is particularly reliable and easy to install whose control unit and electric battery are implanted.

However, it is observed that the most recent pumps operate at a substantially constant rate without real adjustment to the instantaneous needs of the patient and to his or her physical activity.

Furthermore, the life of the implant battery is shorter than an external battery which means more regular recharges thereof.

Although this recharge can be done possibly by percutaneous transduction, it constitutes recurring and distressing constraint for the patient.

There is therefore a pressing need for a method for adjusting an implanted cardiac pump that makes it possible to optimize its electrical consumption in order to increase the time interval between two recharges.

OBJECT OF THE INVENTION

The present invention aims to overcome the drawbacks of the prior art and to address the abovementioned constraints by proposing a method for managing an implantable cardiac pump, that is simple in its design and in its operating mode, reliable and that makes it possible to adjust the setting of this pump to the natural beating of the heart of an individual.

Another object of the present invention is such a method which allows the cardiac pump to respond in real time to the physical efforts of this individual.

Another object of this invention is such a method allowing an operation of the cardiac pump in continuous mode in case of failure of the heart of this individual.

The present invention also targets an implantable management unit comprising a central unit and a power source of a cardiac pump, this central unit comprising software making it possible to set this pump to the natural operation of the heart of the individual.

BRIEF DESCRIPTION OF THE INVENTION

To this end, the invention relates to a method for managing a cardiac pump intended to assist the heart of a patient, said cardiac pump being intended to send pressurized blood at a flow rate proportional to the speed of rotation $V_{rpm}$ of said pump through the aortic valve of said heart.

According to the invention, the following steps are performed, during a same ventricular systole:

(a) detecting the closing of the mitral valve of said heart, the speed of rotation $V_{rpm}$ of said pump being strictly less than a maximum value $V_{rpm\ max}$ of the speed of rotation of said pump, (b) increasing the speed of rotation $V_{rpm}$ of said pump such that, at an instant $t_2$, after the instant $t_1$ corresponding to the closing of said mitral valve, the speed of rotation of said pump is equal, or substantially equal, to said maximum value $V_{rpm\ max}$ of the speed of rotation, (c) keeping said speed of rotation $V_{rpm}$ of said pump at this maximum value $V_{rpm\ max}$ for at least a portion of the time period T for which the aortic valve is open, and optionally repeating the steps (a) to (c) for at least the ventricular systole of a next cardiac cycle.

Advantageously, this management method thus allows a "physiological" setting of the cardiac pump, that is to say a setting as close as possible to the natural operation of the heart of the patient.

The cardiac pump reaches its maximum rotation speed value only to supply the force necessary to eject blood through the aorta and remains, preferably, at a minimum value outside of this phase in order to keep a speed of rotation of the pump constant and to limit its electrical consumption.

In the step (a), there is therefore an effort to determine the start of the period of isovolumetric contraction, the artificial cardiac pump not being at its maximum rotation speed value but at a strictly lower value, and even better, at its minimum rotation speed value.

In the step (c), the speed of rotation $V_{rpm}$ of the pump is kept at a value equal or substantially equal to the maximum value $V_{rpm\ max}$ of the speed of rotation of the pump. During this time period T, the speed of rotation $V_{rpm}$ of the pump is, consequently, constant, or substantially constant.

Obviously, after the step c), an additional step d) is preferably carried out in which the speed of rotation of the pump is reduced such that the speed of rotation $V_{rpm}$ of said pump is strictly less than the maximum value $V_{rpm\ max}$ of the speed of rotation of said pump.

Such a cardiac pump is generally implanted in the ventricle dedicated to the blood circulation to supply the body of the patient with oxygen through the aortic valve. This role is normally devolved to the left ventricle. It may be, in rare cases, that it is the right ventricle which ensures this function. For this reason, "mitral valve" will be understood here to mean the input valve of the ventricle, that is to say the atrioventricular valve. Similarly, "aortic valve" will be understood to mean the output valve of the ventricle, that is to say the sigmoid valve.

In different particular embodiments of this method, each having its particular advantages and being open to numerous possible technical combinations:

at an instant $t_3$ corresponding to the closing, or substantially to the closing, of the aortic valve, an additional step (d) is carried out consisting in reducing the speed of rotation $V_{rpm}$ of said pump to a value strictly less than the maximum value $V_{rpm\ max}$ of the speed of rotation of said pump.

Advantageously, the speed of rotation $V_{rpm}$ of the cardiac pump at the end of the step (d) is equal, or substantially equal, to the speed of rotation $V_{rpm}$ of said pump in the step (a).

Preferably, this cardiac pump is set such that its speed of rotation $V_{rpm}$ is equal, or substantially equal, to a setpoint value outside of the steps b) to d). Advantageously, this setpoint value corresponds to a minimum value $V_{rpm\ min}$ of the speed of rotation of said pump.

This minimum speed $V_{rpm\ min}$ is then determined so as to keep the blood present in the ventricle in motion and prevent the formation of blood clots while minimizing the electrical consumption of the motor of the cardiac pump.

The maximum $V_{rpm\ max}$ and/or minimum $V_{rpm\ min}$ values of the speed of rotation of the pump are preferably limited to predefined and adjustable values. The maximum value $V_{rpm\ max}$ of the speed of rotation is thus not necessarily equal to the maximum speed of rotation that this cardiac pump can achieve. On the contrary, this maximum value $V_{rpm\ max}$ may depend on physiological parameters of the patient and then be a percentage of this maximum speed of rotation of the pump.

Prior to the step (a), the electrical activity of the heart is measured to detect a ventricular depolarization of said heart and in that, from the instant $t_0$ corresponding to the detection of said depolarization, the steps a) to c) are carried out in succession.

Thus, the measurement of the depolarization of the heart advantageously makes it possible to synchronize the different steps of the method on the real cardiac activity of the heart of the patient. From this instant $t_0$ corresponding to the detection of the ventricular depolarization, a detection window is opened that has a predefined duration for detecting the closing of the mitral valve. This detection is preferably performed by measuring audible mechanical vibrations and/or inaudible mechanical vibrations linked to the mechanical activity of the heart. The measurement of these mechanical vibrations makes it possible to generate signals which are then analyzed in order to detect the signal or signals linked to the closing of the mitral valve. This measurement is performed by means of one or more vibration sensors chosen from among a microphone, an accelerometer and combinations of these elements.

Preferably, the measurement of these vibrations linked to the mechanical activity of the heart is performed at an instant $t'_0 = t_0 + t_{blanking}$ after the instant $t_0$. The time delay duration $t'_0 - t_0$ is adjustable and determined so as to minimize or eliminate spurious noises linked to the mechanical activity of the heart in order to facilitate the detection of the closing of the mitral valve.

Advantageously, the measurement of the electrical activity of the heart is performed by means of at least one ventricular electrode. This electrode is in contact with the ventricular wall. It can be placed on the inner or outer surface of said ventricular wall.

The step of detection of the closing of the mitral valve is performed by means of at least one implantable accelerometer.

The implementation of one or more implantable accelerometers makes it possible to detect the inaudible mechanical vibrations linked to the mechanical activity of the heart. This accelerometer is preferably placed inside the ventricle as close as possible to the mitral valve to determine the incident with great accuracy and reliability.

In the step (a) and/or in the step (d), the speed of rotation $V_{rpm}$ of said pump is varied progressively.

The cardiac pump comprising an electric motor powered by a power source such as a rechargeable and implantable battery, a gradual increase in the speed of rotation of the pump to bring the latter from a minimum value Vrpm min to a maximum valve Vrpm max of the speed of rotation advantageously makes it possible to minimize the energy consumption and consequently to increase the period of use of the power source before a recharge.

With the opening of the aortic valve of said heart occurring physiologically at an instant $t_{physio}$, after the instant $t_1$, the time $\Delta t$ separating the instants $t_1$ and $t_2$ is determined, in the step (b), such that said maximum value $V_{rpm\ max}$ of the speed of rotation of said pump is reached before, at, or even after the instant $t_{physio}$.

Advantageously, the speed of rotation $V_{rpm}$ of said pump being reached before the instant $t_{physio}$, an early opening of the aortic valve of the heart is provoked.

Preferably this time $\Delta t$ is equal to, or is substantially equal to, the duration of the isovolumtric contraction phase.

Having previously determined the duration of the isovolumetric contraction phase for said patient by echography or by magnetic resonance imaging (MRI) or even by positron emission tomography, in the step (b), a time $\Delta t$ is taken that is equal to, or substantially equal to, this duration of the isovolumetric contraction phase.

The method is thus simplified by limiting the number of measurements necessary to the performance thereof.

The maximum value $V_{rpm\ max}$ of the speed of rotation of said pump being adjustable, this maximum value $V_{rpm\ max}$ is varied for a given patient as a function of his or her heart rate and/or of the content of the corresponding ventricle.

Thus, when the heart rate of the patient increases, this maximum value $V_{rpm\ max}$ increases also. Similarly, for an increased volume of blood in the ventricle for example following an additional time of rest, the maximum value $V_{rpm\ max}$ of the speed of rotation of the pump is increased to eject more blood through the aortic valve.

The speed of rotation of said cardiac pump is monitored and regulated.

Advantageously, this regulation of the speed of rotation of the pump is performed, in particular in the step (b) and/or the step (d), to avoid the appearance of peaks in the speed of rotation of the pump. The regulation of the speed of rotation of this pump can be performed according to a logic, either in open loop mode (by measuring and programming the end of the systole (closing of the aortic valve)), or in closed loop mode through the implementation of an accelerometer capable of detecting the mitral closing noise but also the aortic closing noise signaling the end of the ventricular systole.

Measuring the electrical activity of the heart, and having determined, from this measurement, a heart rate disorder, the steps a) to c) are performed once in every two consecutive ventricular systoles, the speed of rotation $V_{rpm}$ of said pump being kept at a minimum value $V_{rpm\ min}$ during the so-called rest intermediate systole.

This keeping of the speed of rotation $V_{rpm}$ of the cardiac pump at its minimum value $V_{rpm\ min}$ is performed throughout this intermediate systole, also called rest systole.

Measuring the electrical activity of the heart and having determined, from this measurement, that the patient exhibits a ventricular tachycardia or a cardiac arrest, the speed of rotation $V_{rpm}$ of the pump is kept constantly at its maximum value $V_{rpm\ max}$, independently of the steps a) to c).

Said cardiac pump is an implantable ventricular assistance device (VAD).

This cardiac pump is advantageously anchored to the wall of the heart, the patient then being able to move around actively without risk.

The present invention relates also to a computer program comprising instructions suitable for implementing each of the steps of the management method as described previously, when this program is run on a computer.

Obviously, the expression "computer program" is synonymous with the terms "program" and "software". Similarly, the term "computer" is understood to mean any programmable device. In a particular embodiment, this programmable device can be implanted in the body of the patient and is advantageously powered by an implanted power source such as a rechargeable electric battery, such that this device operates autonomously to set the artificial cardiac pump.

The present invention also relates to an implantable management unit. According to the invention, this management unit comprises a power source and a central unit comprising a processor, said power source being intended to power a cardiac pump, said central unit comprising a set of software instructions which, when they are executed by said processor, make it possible to implement a method for managing said cardiac pump, said cardiac pump being intended to send pressurized blood at a flow rate proportional to the speed of rotation $V_{rpm}$ of said pump, said method comprising, during a same ventricular systole, the following steps:

(a) detecting the closing of the mitral valve of said heart, the speed of rotation $V_{rpm}$ of said pump being strictly less than a maximum value $V_{rpm\ max}$ of the speed of rotation of said pump, (b) increasing the speed of rotation $V_{rpm}$ of said pump such that, at an instant $t_2$, after the instant $t_1$ corresponding to the closing of said mitral valve, the speed of rotation of said pump is equal, or substantially equal, to said maximum value $V_{rpm\ max}$ of the speed of rotation, (c) keeping said speed of rotation $V_{rpm}$ of said pump at this maximum valve $V_{rpm\ max}$ for at least a portion of the time period T for which the aortic valve is open, and optionally repeating the steps (a) to (c) for at least the ventricular systole of a next cardiac cycle.

This management unit is preferably linked to the artificial cardiac pump via a wired link to power this pump and send the control signals thereof.

It can also comprise a wireless transceiver for automatically transmitting data such as information on the heart rate or even the state of the implanted power source, for the purpose of telemedicine follow-up.

The transmission of the data can be performed to a portable external terminal by means of short range wireless communication signals, for example based on a Bluetooth or Zigbee protocol. This external terminal can comprise a communication means implementing a cellular access network and/or an internet network for transmitting these data for example to a cardiologist. The cellular access network can be of several types (2G, 3G, 4G), each type of network being accessible according to several cellular access technologies (2G: EDGE, GPRS, 3G: UMTS, HSDPA, HSUPA, HSPA, HSPA+, 4G: LTE). The internet network is for example a network comprising wireless non-cellular access points such as a WLAN network, for example Wi-Fi or WiMAX or even a Li-Fi network. This external terminal can have a display device to allow the user to read messages or to choose options in a menu.

Preferably, this central unit comprises one or more inputs for receiving one or more signals, each of which is linked to an audible or inaudible mechanical vibration linked to the mechanical activity of the heart, said central unit comprising a first subset of software instructions of said set of software instructions which, when they are executed by said processor, make it possible to define a time window for measuring said signal or signals, for analyzing each signal thus received at the input of said central unit during the time window to determine one or more parameters of the corresponding signal, to compare the parameter or parameters of each duly determined signal with one or more data previously stored in a storage unit of said central unit in order to identify the signal corresponding to the closing of the mitral valve and the instant $t_1$ corresponding to the closing of said mitral valve.

Advantageously, the electrical activity of the heart being measured by means of one or more electrodes, the measurement signal or signals being received at one or more other inputs of said central unit, said central unit comprising a second subset of software instructions of said set of software instructions which, when they are executed by said processor, make it possible to determine in real time the heart rate of the heart of said patient, to control said cardiac pump according to a predetermined law which is a function of said duly determined heart rate, in particular its speed of rotation $V_{rpm}$.

Preferably, said software instructions of said second subset also make it possible, when they are executed by said processor, to determine, from a measurement of the electrical activity of the heart, each instant $t_0$ at which a depolarization a ventricular depolarization of said heart occurs in order to synchronize the steps a) to c) of said management method.

It is consequently possible to synchronize the setting of the cardiac pump on the natural rate of the heart of the patient equipped with this pump.

BRIEF DESCRIPTION OF THE DRAWINGS

Other advantages, aims and particular features of the present invention will emerge from the following description, given, for explanatory and nonlimiting purposes, in light of the attached drawings, in which.

DETAILED DESCRIPTION OF EMBODIMENTS OF THE INVENTION

First of all, note that the figures are not to scale.

Figure 1:
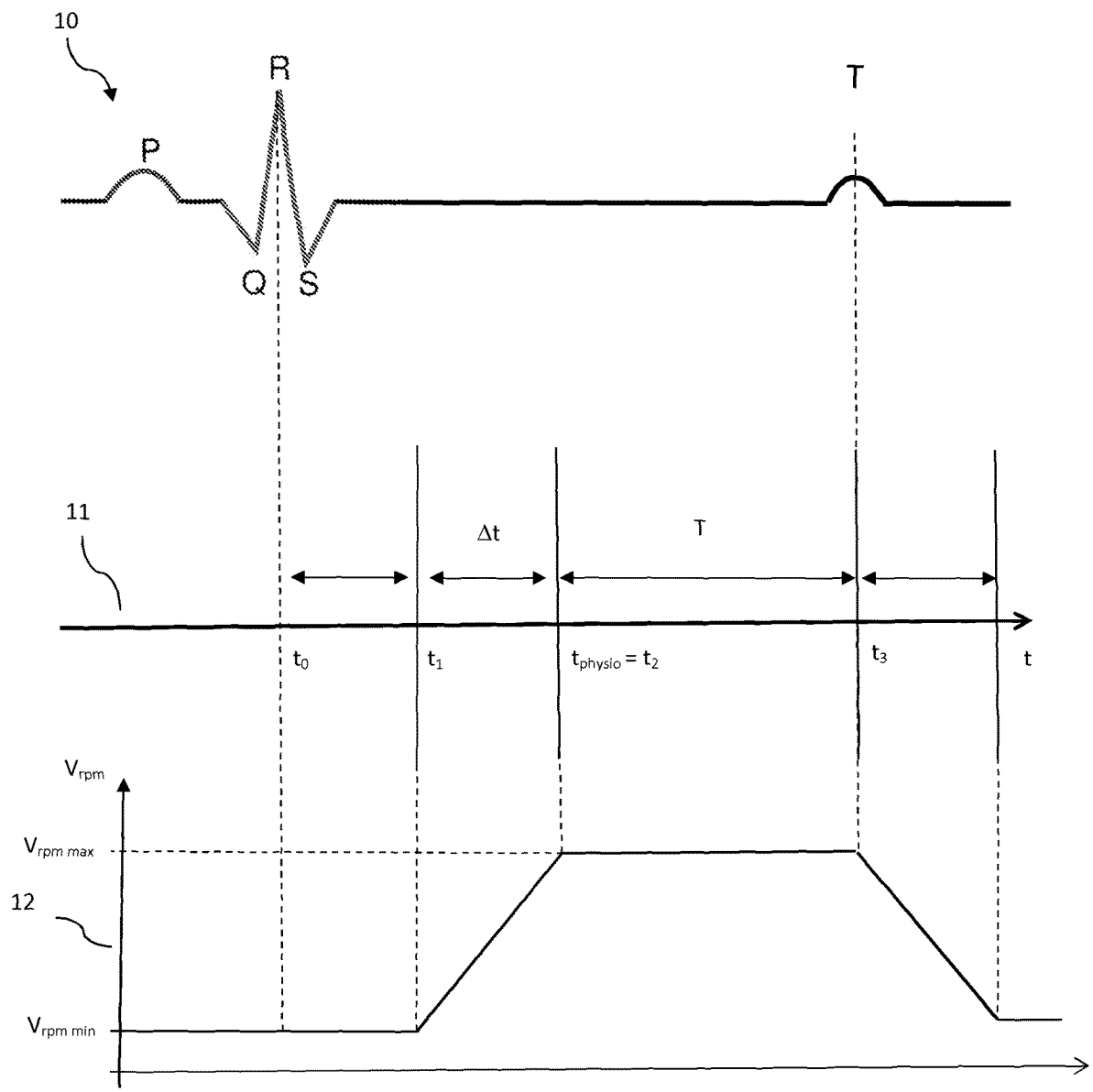
FIG. 1 schematically represents the different steps of the method for managing a cardiac pump as a function of the natural mechanical activity of the heart of an individual.
Figure 2:
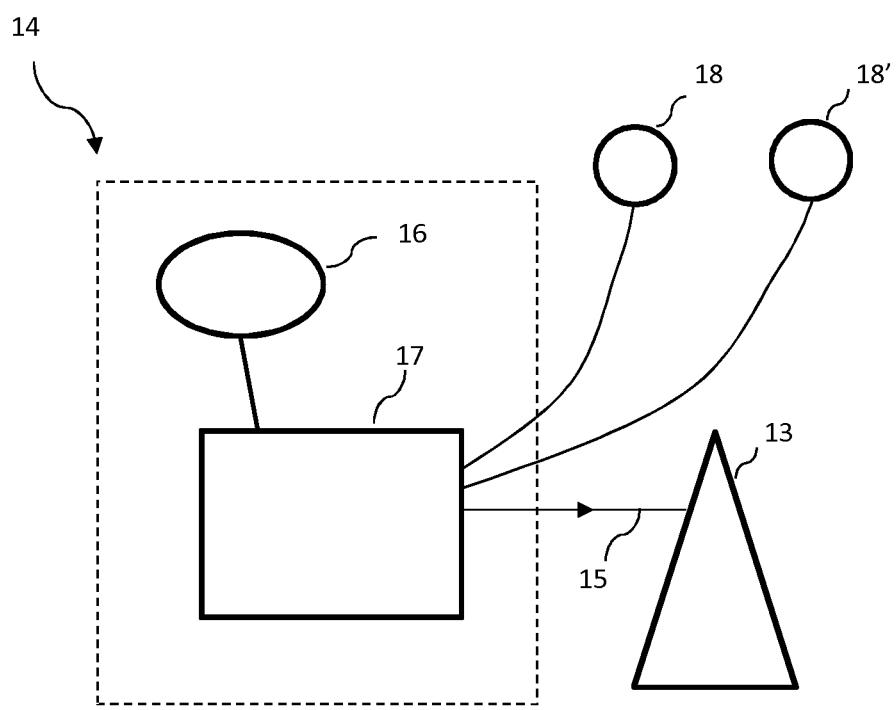
FIG. 2 schematically represents a setting and power supply assembly of an artificial cardiac pump according to a particular embodiment of the invention.

FIG. 1 schematically shows the different steps of the method for managing a cardiac pump as a function of the natural mechanical activity of the heart of an individual, according to a particular embodiment of the present invention.

It is known that the contraction of the heart at rest follows an invariable sequence that can be followed by measuring the electrical activity of the heart. A curve 10 is then obtained of electrical signal as a function of time.

The curve 10 which schematically represents the normal electrical activity of a human heart, essentially shows the wave P denoting the contraction of the atria of the heart, the QRS complex embodying the contraction of the ventricles and the wave T relating to the electrical repolarization of the ventricles.

This electrical activity of the heart finds its corollary in the mechanical activity of the heart which will now be described for just the left ventricle of the heart with respect to a time axis 11.

Initially, the left atrium fills with blood, the pressure therein being greater than the pressure in the left ventricle. Then, the left atrium contracts (wave P) and forces the passage of the blood to the left ventricle, the mitral valve opening to free this passage. After the time interval separating P and R, the left ventricle begins to contract, the pressure increasing and exceeding the pressure in the left atrium, the mitral valve recloses at the instant $t_1$.

However, the pressure in the left ventricle is not yet sufficient to open the aortic valve, the volume of the ventricular cavity not changing, so the term isovolumetric contraction applies.

The pressure then continues to rise in the left ventricle until the aortic valve opens at an instant $t_{physio}$, after the instant $t_1$, to allow the blood contained in the left ventricle to be driven to the bodily circulation during a so-called ejection phase.

This contraction phase ends with the closing of the aortic valve when the pressure in the left ventricle becomes lower than the arterial pressure is called the ventricular systole (time interval situated within the portion of electrical curve Q-T on the curve 10).

The heart is, here, provided with a cardiac pump 13 making it possible to assist the weakened left ventricle in projecting the blood from the left ventricle through the aortic valve.

This cardiac pump 13 is intended to send pressurized blood at a flow rate proportional to the speed of rotation $V_{rpm}$ of this pump 13 through the aortic valve.

This artificial pump 13 here comprises an impeller inserted into the left ventricle through the heart wall, a sealing membrane making it possible to ensure a tight link for the impeller and the wall of the heart, this membrane being partly sutured onto the outer wall of the heart, with a casing secured, directly or indirectly, to the sealing membrane, this casing being placed in the left ventricle and with an electric motor intended to suck and discharge the blood from the bottom of the left ventricle.

A management unit 14 making it possible to control this pump 13 is linked to the impeller by a wired link 15.

This management unit 14 comprises an electrical power source 16 for powering this pump 13 and a central unit comprising processor and a storage unit. This central unit 17 also comprises a set of software instructions which, when they are executed by this processor, make it possible to implement a method for managing this cardiac pump 13.

This management method here comprises a first step aiming to detect the instant $t_1$ corresponding to the closing of the mitral valve, the speed of rotation $V_{rpm}$ of said pump 13 being kept at a value strictly less than a maximum value $V_{rpm\ max}$ of the speed of rotation of the pump 13.

As represented in the curve 12, which shows the variation of the speed of rotation of the pump 13 as a function of time t, this speed of rotation value is equal to a minimum value $V_{rpm\ min}$ of the speed of rotation, which is determined to avoid any stagnation of the blood in the ventricle while minimizing the electrical consumption of the pump 13.

Then, from this instant $t_1$, the speed of rotation $V_{rpm}$ of the pump 13 is increased such that, at an instant $t_2$, after the instant $t_1$, the speed of rotation of the pump 13 is equal, or substantially equal, to its maximum rotation speed value $V_{rpm\ max}$.

Preferably, this increase in the speed of rotation of the pump 13 is progressive so as not to draw energy abnormally from the power source 16.

The instant $t_2$ is chosen here such that it corresponds to the opening of the aortic valve, the pump 13 having thus reached its maximum rotation speed value $V_{rpm\ max}$ to eject the blood through the aortic valve.

As represented in FIG. 1, the speed of rotation of the pump 13 is then kept constant, and at this maximum value $V_{rpm\ max}$, throughout the time period T during which the aortic valve is open so as to ensure a maximum ejection of the blood present in the left ventricle.

When the aortic valve closes, that is to say at the instant $t_3$, the speed of rotation of the cardiac pump 13 is progressively reduced to its minimum value $V_{rpm\ min}$.

Preferably, all of these steps are repeated for each next ventricular systole so as to optimize the energy of the power source 16 and reduce the time between two successive recharges of this power source 16.

It has been observed that this method provided a significant advance in quality of life of the patient suffering from a cardiac insufficiency.

Preferably, and to adapt automatically to the physical activities of the patient, equipped with such a cardiac pump 13, the electrical activity of the heart of this patient is measured so as to detect, prior to the performance of each first step of detection of the closing of the mitral valve, a ventricular depolarization of the heart of the patient.

This depolarization measurement is performed through one or more ventricular electrodes 18, 18'.

Such a measurement advantageously makes it possible to synchronize the different steps of the management method relative to the heart rate of the patient.

Furthermore, and to address the metabolic needs of the patient, in the event of an effort, the maximum value $V_{rpm\ max}$ of the speed of rotation of the pump is adjustable and can therefore be increased to ensure a greater blood flow when necessary.

The invention claimed is:

1. A method for managing a cardiac pump configured to assist the heart of a patient, said cardiac pump being configured to send pressurized blood at a flow rate proportional to the speed of rotation $V_{rpm}$ of said pump through the aortic valve of said heart, the method comprising:
   measuring electrical activity of the heart to detect a ventricular depolarization of the heart; and
   from an instant $t_o$ corresponding to the detecting of the depolarization, the following steps are carried out in succession, during a same ventricular systole:
   (a) detecting the closing of the mitral valve of said heart, the speed of rotation $V_{rpm}$ of said pump being strictly less than a maximum value $V_{rpm\ max}$ of the speed of rotation of said pump,
   (b) from an instant $t_1$, increasing the speed of rotation $V_{rpm}$ of said pump such that, at an instant $t_2$, after the instant $t_1$ corresponding to the closing of said mitral valve, the speed of rotation of said pump is equal, or substantially equal, to said maximum value $V_{rpm\ max}$ of the speed of rotation, the time $\Delta t$ separating the instants $t_1$ and $t_2$ being determined such that said maximum value $V_{rpm\ max}$ of the speed of rotation of the pump is reached before or at an instant $t_{physio}$, $t_{physio}$ being the instant, after the instant $t_1$, when opening of the aortic valve physiologically occurs, and
   (c) keeping said speed of rotation $V_{rpm}$ of said pump at the maximum value $V_{rpm\ max}$ for at least a portion of the time period T during which the aortic valve is open.

2. The method as claimed in claim 1, wherein, at an instant $t_3$ corresponding to the closing or substantially to the closing of the aortic valve, an additional step (d) is carried out including reducing the speed of rotation $V_{rpm}$ of said pump to a value strictly less than the maximum value $V_{rpm\ max}$ of the speed of rotation of said pump.

3. The method as claimed in claim 2, wherein said pump is set such that a speed of rotation $V_{rpm}$ of the pump is equal, or substantially equal, to a setpoint value outside of the steps b) to d).

4. The method as claimed in claim 3, wherein said setpoint value corresponds to a minimum value $V_{rpm\ min}$ of the speed of rotation of said pump.

5. The method as claimed in claim 1, wherein the step of detection of the closing of the mitral valve is performed by at least one implantable accelerometer.

6. The method as claimed in claim 2, wherein, in the step (a) and/or in the step (d), the speed of rotation $V_{rpm}$ of said pump is varied progressively.

7. The method as claimed in claim 1, wherein, having previously determined a duration of a phase of isovolumetric contraction for said patient by echography or by magnetic resonance imaging (MRI) or even by positron emission tomography, in the step (b), the time $\Delta t$ is taken that is equal to, or substantially equal to, the duration of the isovolumetric contraction phase.

8. The method as claimed in claim 1, wherein the maximum value $V_{rpm\ max}$ of the speed of rotation of said pump being adjustable, the maximum value $V_{rpm\ max}$ being varied for a patient as a function of a heart rate of the patient and/or of the content of the corresponding ventricle.

9. The method as claimed in claim 1, wherein the speed of rotation of said pump is monitored and regulated.

10. The method as claimed in claim 1, wherein, having determined from the measurement of the electrical activity of the heart a disorder of the heart rate, the steps a) to c) are carried out once in every two consecutive ventricular systoles, the speed of rotation $V_{rpm}$ of said pump being kept at a minimum value of $V_{rpm\ min}$ during the rest systole.

11. The method as claimed in claim 1, wherein, having determined from the measurement of the electrical activity of the heart that the patient presents a ventricular tachycardia or a cardiac arrest, the speed of rotation $V_{rpm}$ of the pump is kept constantly at the maximum value $V_{rpm\ max}$, independently of the steps a) to c).

12. The method as claimed in claim 1, wherein said cardiac pump is an implantable ventricular assistance device (VAD).

13. A computer program comprising instructions suitable for implementing each of the steps of the method as claimed in claim 1, when said program is run on a computer.

14. A management unit, comprising:
   a power source configured to power a cardiac pump; and
   a central unit (17) comprising a processor, said central unit comprising a set of software instructions which, when executed by said processor, enable implementing a method for managing said cardiac pump, said cardiac pump being configured to send pressurized blood at a flow rate proportional to the speed of rotation $V_{rpm}$ of said pump, said method comprising:
   measuring electrical activity of the heart to detect a ventricular depolarization of the heart, and
   from an instant $t_o$ corresponding to the detecting of the depolarization, the following steps are carried out in succession, during a same ventricular systole:
   (a) detecting the closing of the mitral valve of said heart, the speed of rotation $V_{rpm}$ of said pump being strictly less than a maximum value $V_{rpm\ max}$ of the speed of rotation of said pump (13),
   (b) from an instant $t_1$, increasing the speed of rotation $V_{rpm}$ of said pump (13) such that, at an instant $t_2$, after the instant $t_1$ corresponding to the closing of said mitral valve, the speed of rotation of said pump is equal, or substantially equal, to said maximum value $V_{rpm\ max}$ of the speed of rotation, the time $\Delta t$ separating the instants $t_1$ and $t_2$ being determined such that said maximum value $V_{rpm\ max}$ of the speed of rotation of the pump is reached before or at an instant $t_{physio}$, $t_{physio}$ being the instant, after the instant $t_1$, when opening of the aortic valve physiologically occurs, and (c) keeping said speed of rotation $V_{rpm}$ of said pump at the maximum valve $V_{rpm\ max}$ for at least a portion of the time period T for which the aortic valve is open.

15. The unit as claimed in claim 14, wherein said central unit comprises one or more inputs configured to receive one or more signals, each of the inputs being linked to an audible or inaudible mechanical vibration linked to mechanical activity of the heart, a first subset of software instructions of said set of software instructions which, when executed by said processor, enables defining a time window for measuring said signal or signals, for analyzing each signal thus received at the input of said central unit during the time window to determine one or more parameters of the corresponding signal, for comparing the parameter or parameters of each signal thus determined with one or more data previously stored in a storage of said central unit in order to identify the signal corresponding to the closing of the mitral valve and the instant $t_1$ corresponding to the closing of said mitral valve.

16. The unit as claimed in claim 14, wherein the electrical activity of the heart is measured by one or more electrodes, the measurement signal or signals being received at one or more other inputs of said central unit, said central unit comprising a second subset of software instructions of said set of software instructions which, when executed by said processor, enables determining in real time the heart rate of the heart of said patient, to monitor said cardiac pump according to a predetermined law which is a function of said duly determined heart rate, in particular a speed of rotation $V_{rpm}$.

17. The unit as claimed in claim 16, wherein said software instructions of said second subset, when executed by said processor, enable determining, from the measurement of the electrical activity of the heart, each instant to at which a ventricular depolarization of said heart occurs in order to synchronize the steps a) to c) of said management method.

* * * * *